(12) United States Patent
Neuland et al.

(10) Patent No.: US 7,232,500 B2
(45) Date of Patent: Jun. 19, 2007

(54) METHOD AND DEVICE FOR PRODUCING PRODUCTS IN WEB FORM

(75) Inventors: Detlev Neuland, Wangen-Neuravensburg (DE); Wolfgang Schaefer, Madison, NJ (US); Peter Schwarz, Koenigswinter (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 33 days.

(21) Appl. No.: 10/501,806

(22) PCT Filed: Jan. 15, 2003

(86) PCT No.: PCT/EP03/00334

§ 371 (c)(1),
(2), (4) Date: Jul. 20, 2004

(87) PCT Pub. No.: WO03/061635

PCT Pub. Date: Jul. 31, 2003

(65) Prior Publication Data

US 2005/0095363 A1 May 5, 2005

Related U.S. Application Data

(60) Provisional application No. 60/351,745, filed on Jan. 25, 2002.

(51) Int. Cl.
| | |
|---|---|
| *B32B 38/10* | (2006.01) |
| *B32B 37/08* | (2006.01) |
| *B32B 38/16* | (2006.01) |
| *B65H 81/00* | (2006.01) |
| *B29C 65/02* | (2006.01) |
| *B65H 75/02* | (2006.01) |
| *D04H 3/16* | (2006.01) |

(52) U.S. Cl. .............. 156/247; 156/171; 156/192; 156/273.3; 156/443; 156/498

(58) Field of Classification Search ............ 156/247, 156/249, 166, 171, 184, 191, 192, 272.2, 156/273.3, 283, 284, 290, 297, 300, 302, 156/308.2, 308.4, 320, 324, 344, 443, 498, 156/499

See application file for complete search history.

(56) References Cited

U.S. PATENT DOCUMENTS

| 2,820,716 A | * | 1/1958 | Harmon et al. ............. 427/474 |
| 3,444,858 A | | 5/1969 | Russell ..................... 128/260 |

(Continued)

FOREIGN PATENT DOCUMENTS

| CA | 492 040 | 4/1953 | .................. 267/93 |

(Continued)

*Primary Examiner*—Chris Fiorilla
*Assistant Examiner*—Sonya Mazumdar
(74) *Attorney, Agent, or Firm*—ProPat, L.L-C7

(57) ABSTRACT

This invention pertains to methods and devices for producing products in web form. In particularly advantageous embodiments, the instant invention relates to methods and devices for forming films by coating a coating mass formed from organic raw materials in an aqueous basis onto a reusable transfer support web to form a composite. The composite is then dried and the dried coating transferred onto a intermediate support material. The dried coating and intermediate support material are directed to a winding station. Upon separation from the dried coating, the dried reusable transfer support web may be directed to treatment and cleaning stations and is subsequently reused.

16 Claims, 1 Drawing Sheet

U.S. PATENT DOCUMENTS

| | | | | |
|---|---|---|---|---|
| 3,518,152 | A | * | 6/1970 | Storti .......................... 156/540 |
| 3,823,209 | A | * | 7/1974 | Birckhead, Jr. et al. .... 264/462 |
| 3,859,157 | A | * | 1/1975 | Morgan ...................... 156/268 |
| 3,869,328 | A | * | 3/1975 | Instance ..................... 156/285 |
| 4,128,445 | A | | 12/1978 | Sturzenegger et al. ........ 156/64 |
| 4,473,422 | A | * | 9/1984 | Parker et al. ................ 156/233 |
| 4,849,246 | A | | 7/1989 | Schmidt ......................... 427/2 |
| 4,913,760 | A | * | 4/1990 | Benson et al. ......... 156/244.11 |
| 5,006,189 | A | * | 4/1991 | Tsukamoto et al. .......... 156/247 |
| 5,047,244 | A | | 9/1991 | Sanvordeker et al. ....... 424/435 |
| 5,863,628 | A | * | 1/1999 | Barry ....................... 428/40.1 |
| 5,891,290 | A | | 4/1999 | Deurer et al. ................ 156/249 |
| 6,090,238 | A | * | 7/2000 | Smith ......................... 156/344 |

FOREIGN PATENT DOCUMENTS

| | | |
|---|---|---|
| DE | 24 49 865 A1 | 4/1976 |
| DE | 36 30 603 A1 | 3/1988 |
| EP | 0 219 762 A1 | 4/1987 |
| EP | 0 460 588 A1 | 12/1991 |
| WO | WO 00/67694 A1 | 11/2000 |
| WO | WO 01/28904 A1 | 4/2001 |

* cited by examiner

METHOD AND DEVICE FOR PRODUCING PRODUCTS IN WEB FORM

CROSS REFERENCE TO RELATED APPLICATIONS

This application is being filed under rule 1.371 National Stage Application of pending International Application No. PCT/EP03/00334, filed Jan. 15, 2003, which claims priority to the following provisional application: U.S. Patent Application No. 60/351,745, filed Jan. 25, 2002.

FIELD OF THE INVENTION

The present invention pertains to a method and a device for producing products in web form, in particular, thin films by coating a coating mass comprising organic raw materials in an aqueous basis on a reusable support web, drying the products and transferring the dried products onto a reusable intermediate support material.

BACKGROUND OF THE INVENTION

Flat administration forms to be applied in the oral region and on mucous membranes of the mouth are known. U.S. Pat. No. 3,444,858 describes medicament strips based on a gelatin-like material. Also, pharmaceutical products in the form of a film have already been described in the early 70 s. DE-A 24 49 865 described medicinal active substance carriers in the form of a film, containing different active substances and active substance concentrations.

U.S. Pat. No. 4,128,445 discloses technical solutions in loading of carrier material with active substances and, in this context, goes into the subsequent addition of active substance preparations by applying them onto pre-fabricated film-shaped preparations. The document describes loading methods in dry and moist form aiming at achieving a uniform, subsequent distribution of active substance on a layer.

Canadian patent application No. 492 040 describes a process for manufacture of film-shaped preparations employing active substance along with gelatin, agar, gluten, carboxyvinyl polymer, polyhydric alcohol, vegetable mucilage, wax or water.

Also known are proposals for application of active substance-loaded films or foils outside the pharmaceutical field. Thus, in EP-A 219 762 a water-soluble film of starch, gelatin, glycerol or sorbite is disclosed, which is coated using the roll coating method. In this connection, it is stated that such dosing forms may also be produced employing ingredients of chemical reagents, aromatics and the like.

DE-A 36 30 603 provides for a flat dosage form, on a carrier material (release film), to be peelable in doses.

Drug containing film-shaped systems and their advantages are further known from U.S. Pat. No. 5,047,244. These systems comprise a double-layered structure of a water swellable layer and a non-water-swellable barrier film. The use of polymers such as polyethylene glycol, the use of colloidal silicon dioxide, of bioadhesive (e.g. carboxy-functional) polymers, but also of polyvinyl alcohol, and of a number of other auxiliary substances is likewise known from the above publication.

A preparation suitable for making film-shaped aromatics-containing preparations is described by EP-A 460 588. A composition comprising 20 to 60 weight-% of film former, 2 to 40 weight-% of gel former, 0.1 to 35 weight-% of active substance or aromatic, and a maximum of 40 weight-% of an inert filling agent is regarded as affording particular advantages. As a gel former, polyvinyl alcohol is mentioned besides other ingredients. However, as it turns out, the gel-forming properties of polyvinyl alcohol are only partially compatible with the film formers mentioned in this written document. A portion of 20 weight-%, and more, of film-former—mostly a sugar derivative, polyethylene glycol, etc.—lead to considerable loss of aroma occurring already in thin layer drying, which is part of the production process.

The films or coatings to which the instant invention is related are based on organic raw materials or on a mix of such substances. These are preferably water-soluble substances. Such organic raw materials include polymers such as polyvinyl alcohol, polyvinyl pyrrolidone, cellulose derivatives, polyvinyl acetate, polyetlylene glycol, alginate, carrageenan, xanthan, gelatine and other water-soluble polymers known to the skilled artisan, as well as mixtures and copolymers of such substances. If desired, such films or coatings may also include fillers such as mannitol, lactose, calcium phosphate, glucose, sorbitol etc., active substances such as drugs, aroma substances, menthol etc., sweeteners such as cyclamate, flavours such as glutamate, and other ingredients, including in some cases volatile ingredients. These films may also have mucoadhesive properties.

Usually, the films and coatings are produced by means of casting methods or reverse coating methods. The manufacture of thin films or coatings is accomplished according to the present invention in that initially a coating mass is prepared containing organic substances which are suitable for forming a film, or a coating, for instance, polymers such as polyvinyl alcohol, polyvinyl pyrrolidone, cellulose derivatives, polyvinyl acetate, polyetlylene glycol, alginate, carrageenan, xanthan, gelatine and other water-soluble polymers known to the skilled artisan, as well as mixtures or copolymers of such substances. Preferably, these substances are completely or partially dissolved or dispersed in water. Apart from water, other solvents may be used as well, e.g. alcohols such as methanol, ethanol, propanol or solvent mixtures such as water-alcohol mix.

The coating composition may further comprise various additives, e.g. fillers such as mannitol, lactose, calcium phosphate, glucose, sorbitol etc., and/or active substances such as drugs, aroma substances, menthol etc., and/or sweeteners such as cyclamate, flavours such as glutamate, and other ingredients, including in some cases volatile ingredients.

The coating mass thus obtained is subsequently applied to a web-shaped support material, using the casting method or reverse coating method. As support material, a web or sheet of paper, plastic, metal or a composite of two or more of these materials may be used.

The product web may, for example, have a width of about 0.1 m to about 2 m. Preference is given a width in the range of from 0.5 to 1.6 m. The films or coatings applied to the support layer are preferably thin, that means, their thickness ranges of from about 10 to 500 µm, preferably from 50 to 200 µm.

The coated support material, i.e. the composite of support and coating composition, is thereafter transferred into a drying device (drying oven) and transported through the same, preferably continuously.

The dried composite is then wound up and stored.

The above-described method, however, has the disadvantage that parts of the active-ingredient diffuse from the coating into the support material during the contact period. For that reason, used support material cannot be used again for the preparation of the same or other products in web form, since an unpredictable quantity of active-ingredient disappears from the coating or diffuses back from the support material into the coating during the contact period. Thus, big amounts of waste support material arise during the conventional process making the preparation expensive and environmentally less favourable.

SUMMARY OF THE INVENTION

The object of the present invention was to provide a method and a device for the preparation of products in web form in which reduced amount of waste transfer film occurs, thus, saving costs and environmental effort, as well.

The invention, accordingly, pertains to a method for producing products in web form in which a coating mass first is applied onto the surface of a transfer support web, subsequently the composite of coating mass and transfer support web is dried thermally, then an intermediate support material is applied on the surface of the coating and finally the composite of the intermediate support material and the coating is separated from the transfer support web, wound up and stored, wherein the transfer support web used is preferably an endless loop.

DETAILED DESCRIPTION OF THE INVENTION

Figure 1:
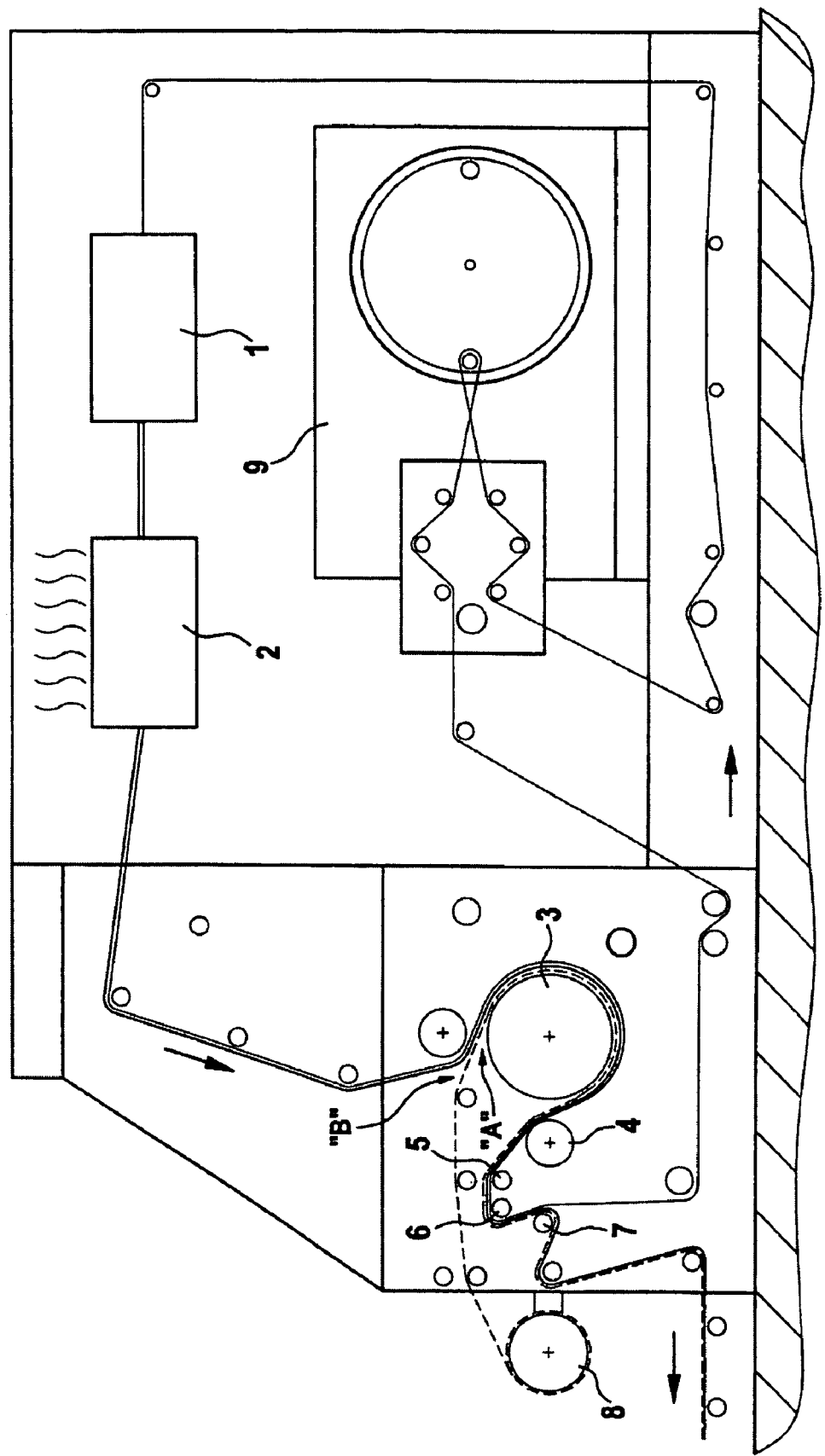
FIG. 1 is a schematic illustration of a side view of an exemplary machine in accordance with the invention.

In the preferred embodiment of the present invention, the transfer support web is comprised of a solid material such as polymer material having sufficient mechanical strength and heat resistance or the transfer film is comprised of a composite material of paper with a polymer layer on top or a metal foil or a composite material of metal and polymer film such as metallized polymer film.

The endless loop used as the transfer support web in the present invention, preferably, has a uniform thickness over its total length to avoid fluctuations in the thickness of the product in web form applied thereon.

The composite of the coating and the transfer support web is dried by thermal treatment in a heating device, preferably in a hot air chamber at temperatures in the range of from 40 to 120° C., preferred from 50 to 100° C. It is also possible to conduct the thermal treatment in multiple steps through multiple heating devices at different temperatures. The total time period for thermal treatment lies within the range of from 5 s to 60 s, preferably from 10 s to 50 s.

After the thermal treatment, the humidity of the product in web form is adjusted in the appropriate range of from about 20 to 60%. The composite is then fed to a laminating- or cooling device, where an intermediate support material coming from a storage roll is applied onto the coating. The intermediate support material is preferably fixed with a strip of an adhesive at the starting point. Possible adhesives are hot melt adhesives or pressure sensitive adhesives which are commercially available. The laminating- or cooling device comprises essentially a cooling drum on which the laminate of intermediate support material, coating and transfer support web is pressed together to maintain a sufficient connection.

The intermediate support material may be comprised of paper or paper like material like cardboard, however, it is also possible to use polymer films as intermediate support material.

Leaving the laminating station the transfer support web is separated from the laminate of intermediate support material, coating and transfer support web by means of rolls. The separation of the transfer support web is easy, if the humidity of the coating is adjusted in the appropriate range.

The ready prepared product in web form comprising the intermediate support material and the coating is wound up and stored for its final destination subsequently after its separation from the transfer support web.

The separated transfer support web, however, is fed to a regeneration station. The regeneration of the transfer support web comprises at least mechanical removal of every adhering foreign particles and vacuum cleaning of the mechanical treated transfer support web. Additionally, the regeneration can be combined with a wet or chemical decontamination comprising washing the transfer support web with clear water or organic solvent or cleaning it with detergents and subsequent drying in hot air. In any case, the regenerated transfer support web is wound up and fed back or alternatively immediately fed back to the coating station, to be applied again with the coating, in this manner circulating endless according to the method of the instant invention.

The present invention pertains also to a device for performing the method producing products in web form according to the transfer method. The device comprises at least a coating station, a laminating or cooling station, separating rolls and a regeneration station for a transfer support web, whereby the transfer support web is performed as an endless loop.

The device in its preferred embodiment is illustrated for the skilled artisan by means of the attached drawing.

FIG. 1 shows, schematically, a machine of the present invention in side view.

Especially, FIG. 1 shows the coating station 1, wherein the coating is applied onto the transfer support web, and the heating device 2, wherein the transfer support web coated with the coating is thermally treated. The heat treated transfer support web applied with the coating reach at the point "A" the lamination station comprising a big cooling drum 3. Simultaneously, an intermediate support material coming from a storage roll 8 is laminated with the coating at point "A". Before reaching point "A", the support layer is fixed with a strip of an adhesive "B", After the cooling drum 3, separating rolls 4, 5, 6 and 7 are arranged. At the last separating roll 7 the transfer support web is separated from the product in web form. The product in web form comprising the intermediate support amterial and the coating is fed to a winding station (not shown), whereas the transfer support web reaches the regeneration station 9 where mechanical treatment and vacuum cleaning occurs. The recirculation of the regenerated transfer support web to the coating station 1 is shown in the right part of the picture, whereas the alternative of winding up and using again of the transfer support web is not illustrated in the picture.

The present invention is a novel and economic method to produce products in web form, especially under cost saving conditions, since a minimum of waste material is caused due to the recirculation of the transfer support web. According to the prior praxis, all used transfer support web had to be disposed of as waste material.

The invention claimed is:

1. A method for producing products in web form comprising
   (i) first applying coating onto a surface of a transfer support web,
   (ii) subsequently drying the composite of transfer support web and coating,
   (iii) adjusting the humidity of the dried composite of transfer support web and coating to about 20 to 60%,
   (iv) then applying an intermediate support material on the coating of the humidity adjusted composite mentioned in step (iii) above,
   (v) finally separating the composite of intermediate support layer and humidity adjusted coating from the transfer support web, and
   (vi) winding up and storing the composite of intermediate support layer and coating,
   wherein the application of the intermediate support material as defined in step (iv) is carried out by feeding said humidity adjusted composite, comprising the coating and the transfer support web, to a cooling station, where said intermediate support material coming from a storage roll is applied onto the coating of said composite.

2. A method according to claim 1, wherein the transfer support web comprises a solid material selected from (i) a polymer material, (ii) a composite material of paper with a polymer layer, (iii) a metal foil, or (iv) a composite material of metal and polymer film.

3. A method according to claim 1, wherein the transfer support web has a uniform thickness over its total length.

4. A method according to claim 1 wherein the coating is prepared by mixing its ingredients in an aqueous medium.

5. A method according to claim 1, wherein the coating is applied to the transfer support web in a coating station by a casting method or a reverse coating method in, a thickness in the range of from 10 to 500 μm.

6. A method according to claim 1, wherein the drying is performed in a hot air chamber at temperatures in the range of from 40 to 120° C.

7. A method according to claim 6 wherein the drying is performed at temperatures in the range of from 50 to 100° C.

8. A method according to claim 1, wherein the intermediate support material is fixed with a strip of an adhesive.

9. A method according to claim 1, wherein the intermediate support material comprises paper, cardboard, or polymer film.

10. A method according to claim 1, wherein the separated transfer support web is fed to a regeneration station, wherein regeneration of the transfer support web is performed.

11. A method according to claim 10, wherein the regeneration of the transfer support web comprises at least mechanical treatment and vacuum cleaning of the mechanically treated transfer support web.

12. A method according to claim 11, wherein the regeneration is combined with a wet or chemical decontamination comprising washing the transfer film with clear water or organic solvent or cleaning it with detergents and drying it in hot air.

13. A method according to claim 10, wherein the regenerated transfer support web is immediately recirculated to the coating station, to be applied again with the coating.

14. A method according to claim 10, wherein the regenerated transfer support web is first wound up and after storage recirculated again to the coating station, to be applied again with the coating.

15. A method for producing products according to claim 1, wherein the coating comprises organic raw materials.

16. A method for producing products according to claim 15, wherein the organic raw material is selected from polyvinyl alcohol, polyvinyl pyrrolidone, a cellulose derivative, polyvinyl acetate, polyethylene glycol, alginate, carrageenan, xanthan, gelatin, mixtures thereof or copolymers thereof.

* * * * *